US00PP18441P2

(12) United States Plant Patent
Berry

(10) Patent No.: US PP18,441 P2
(45) Date of Patent: Jan. 22, 2008

(54) ***LOROPETALUM* PLANT NAMED 'PEACK'**

(50) Latin Name: *Loropetalum chinensis*
Varietal Denomination: Peack

(76) Inventor: James Bryan Berry, 25075 Austin Rd., Daphne, AL (US) 36526

( * ) Notice: Subject to any disclaimer, the term of this patent is extended or adjusted under 35 U.S.C. 154(b) by 0 days.

(21) Appl. No.: 11/297,142

(22) Filed: Dec. 8, 2005

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent Bell
*Assistant Examiner*—June Hwu

(57) ABSTRACT

A new and distinct variety of *Loropetalum* that possesses unique color and growth habit.

1 Drawing Sheet

Latin name: *Loropetalum chinensis.*
Variety denomination: 'Peack'.

BACKGROUND OF THE INVENTION

The present invention relates to a new and distinct variety of *Loropetalum chinensis,* which was discovered as an unusual, distinctive, and ornamentally special seedling of unpatented *Loropetalum chinensis* 'Pizzazz™' at a commercial greenhouse located close to Loxley, Ala., by James Bryan Berry in 2002. The unique characteristics of the new variety 'Peack' will make the plant useful when used as a groundcover in the landscape in appropriate USDA climactic zones. The plant is unlike the species in growth habit.

*Loropetalum chinensis* 'Peack' has been asexually reproduced for four generations by cutting and has demonstrated stability of growth of all phenotypic characteristics from the original plant thru each generation. Asexual reproduction was achieved at a commercial greenhouse in Loxley, Ala. by James Bryan Berry. 'Peack' also has been reproduced by tissue culture in a laboratory in Magnolia, Tex. Thru this propagation process the variety 'Peack' has been reliably stable and true to type for several generations. Both methods of propagation resulted in identical plants to the original 'Peack' plant.

BRIEF DESCRIPTION OF ILLUSTRATION

FIG.#1 Demonstrates the intensity of dark foliage pigmentation and large leaves.

FIG.#2 Demonstrates the mounding habit and landscape application.

DETAILED BOTANICAL DESCRIPTION OF THE PLANT

Color references are made to The Royal Horticulture Society Colour Chart (1995 Edition) and all terminology used is from this color chart. Otherwise descriptive terminology is botanic or ordinary in nature. Plants grown in #1 containers were used for the following descriptions. Plants were grown under normal greenhouse commercial conditions near Magnolia, Tex. The observed plants were 14 months old from date of planting. During the production period day temperatures ranged from 29 to 37 degrees Celsius and night temperatures ranged from 25 to 27 degrees Celsius. Characteristics of plants observed in growing at a commercial nursery near Loxley, Ala. were identical to the plants described. This botanic description was made in November 2005.

Botanical: *Loropetalum chinensis* 'Peack'.
Parentage: Seedling of non-patented *Loropetalum chinensis* 'Pizzazz™'.
Propagation: By vegetative cutting and tissue culture.
Time to initiate roots, summer: 14–20 days at 28° Celsius.
Time to initiate roots, winter: 32–40 days at 20° Celsius.
Time to produce a rooted plant, summer: About 5 months at 28° Celsius.
Time to produce a rooted plant, winter: About 7 months at 20° Celsius.
Plant:
- *Roots.*—Dark red and branching, not fibrous, fleshy.
- *General appearance.*—Dark brown foliage, densely branching. Mounding then spreading habit.
- *Size.*—2' tall and 3.5 to 4.5' wide.
- *Branching.*—Mounding, not erect.
- *Lateral branches.*—Multi-branched shrub.
- *Branch length.*—Averages 30" long, prostrate.
- *Branch surface texture.*—Stellate — pubescent.
- *Branch diameter.*—1.25 centimeters at maturity, typically 1 millimeter or less.
- *Mature branch coloration.*—Greyed-orange group 177A.
- *Immature branch coloration.*—Brown group 200A.
- *Habit.*—Mounding then prostrate.
- *Hardiness.*—USDA Zone 7.
- *Vigor.*—Average.
- *Pests/diseases.*—No pest or disease problems noted.
- *Leaf margin.*—Entire with stellate hairs.
- *Venation.*—Pinnate.
- *Shape.*—Ovate.
- *Arrangement.*—Alternate, simple.
- *Length.*—3.9 centimeters.
- *Width.*—2.9 centimeters.
- *Apex.*—Acute.
- *Leaf base.*—Acute.
- *Texture.*—Upper and lower, pubescent and coarse, non-pliable, impressed veins, underside glacous. Midribs and veins with stellate hairs.
- *Color and top.*—Brown group 200A.

*Underside.*—Gray group 201B.

*Vein and midrib.*—Grayed purple group 185D.

Petioles:

*Length.*—3.2 millimeters.

*Width.*—Approximately 0.7 millimeters.

*Color.*—Brown group 200A.

*Texture.*—Stellate-pubescent.

Internodes:

*Length.*—1.9 centimeters.

*Flowers.*—None observed.

*Reproductive organs.*—None observed.

*Fruit.*—None observed.

Other Data Provided

Comparison with Parent

*Loropetalum chinensis* 'Peack' is unique in growth habit. A four-year-old plant is naturally 1.5 feet tall and 36 inches wide without pruning or shaping. The plant is strongly mounding with branches sharply turning outward and then downward. The parent variety *Loropetalum chinensis* 'Pizzazz™' is not compact but is an upright growing shrub to about 12 feet high and 7 feet wide.

'Peack' is distinctive to another known cultivars because the underside of the leaf is a deep violet. The parent *Loropetalum chinensis* 'Pizzazz™' as well as 'Bill Wallace', U.S. Plant Pat. No. 15,277 all have leaves with undersides that are green. Additionally, the average leaf of the new plant is 50% + wider than the comparative varieties, excluding 'Zhuzhou'.

Comparison to Comparable Cultivars

The following traits are determined to be the unique characteristics of 'Peack'. The traits which cause 'Peack' to be a new and distinct cultivar are:

1. Significantly larger leaf width than the species average
2. Deep, violet (non-green) pigmentation of underside of leaf
3. A mounding and spreading growth habit In side-by-side comparisons, plants of the new *Loropetalum chinensis* 'Peack' differed from plants of the cultivar 'Bill Wallace' in the following ways:

1. Plants of the new cultivar 'Peack' are mounding compared to 'Bill Wallace' which is outwardly spreading with prostate plant growth.
2. Leaves of the new cultivar 'Peack' are large and wide compared to the leaves of 'Bill Wallace', which are narrow and small.
3. The underneath side of the leaves of 'Peack' are deep violet and the underneath sides of the leaves of 'Bill Wallace' are green.

In side-by-side comparisons, plants of the new *Loropetalum chinensis* 'Peack' differed from the non-patented parent cultivar, 'Pizzazz™' in the following ways:

1. Plants of the new cultivar 'Peack' are mounding compared to 'Pizzazz™', which grows strongly upright.
2. Leaves of the new cultivar 'Peack' are larger and wider compared to the leaves of 'Pizzazz™', which are narrower and not as long.
3. The underneath side of the leaves of 'Peack' are deep violet and the underneath sides of the leaves of 'Pizzazz™' are green.

In side-by-side comparisons, plants of the new *Loropetalum chinensis* 'Peack' differed from the cultivar, 'Zhuzhou' in the following way:

1. Plants of the new cultivar 'Peack' are mounding compared to 'Zhuzhou', which grows strongly upright.

SUMMARY OF THE INVENTION

*Loropetalum chinensis* 'Peack' has a unique combination of characteristics. 'Peack' has unusually dark colored foliage, large leaves, and a mounding and spreading growth habit. 'Peack' attributes make it an ideal candidate for landscape use as an intermediate groundcover.

It is claimed:

1. A new and unique variety of *Loropetalum* plant named 'Peack' as herein shown and described.

* * * * *

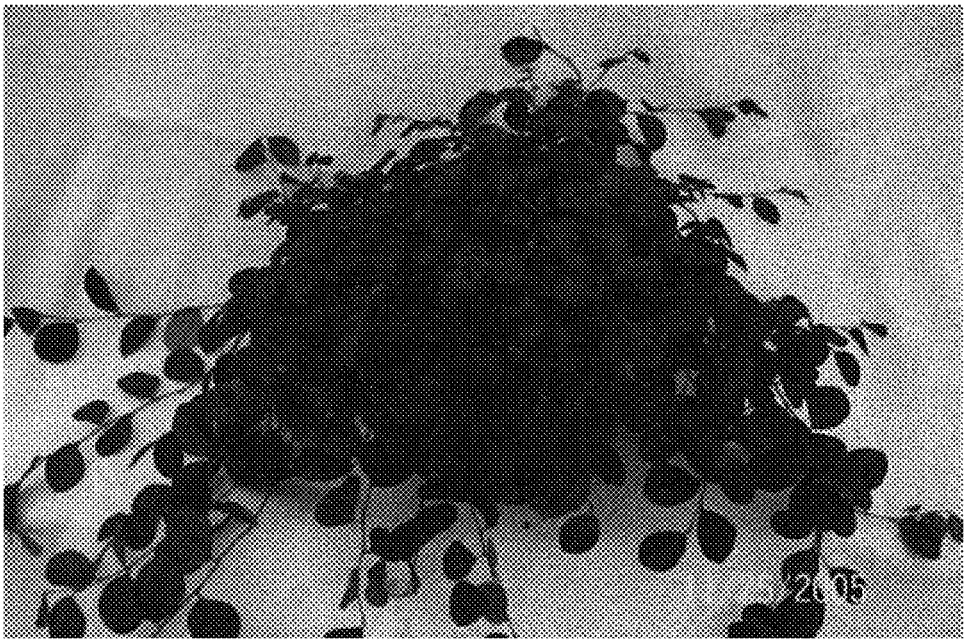
figure one
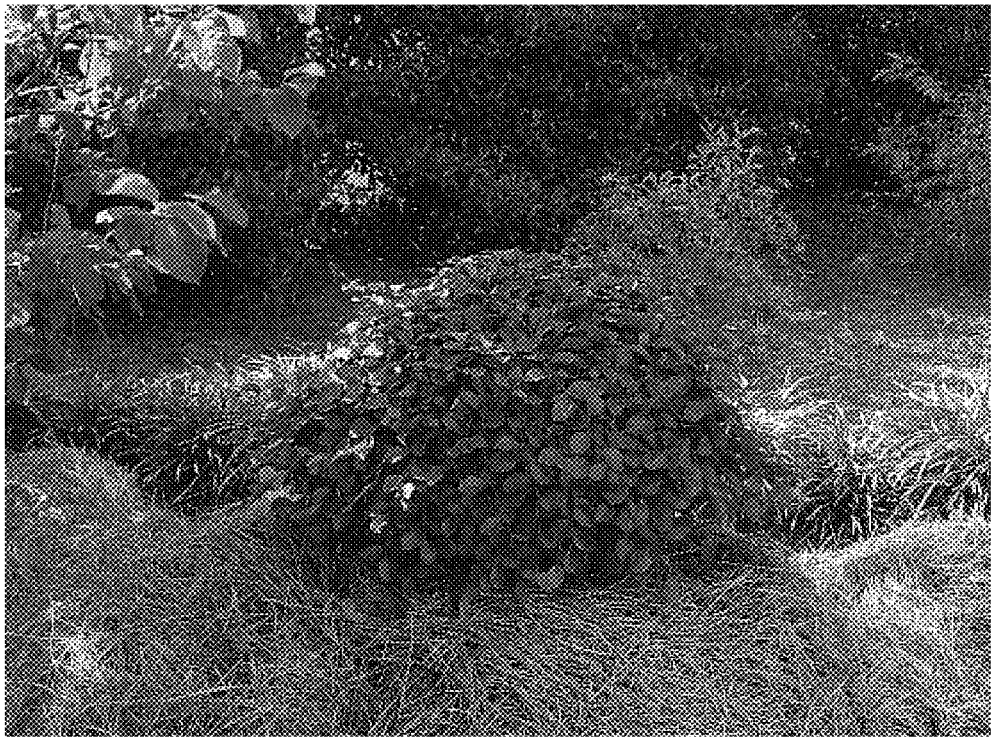
figure two

UNITED STATES PATENT AND TRADEMARK OFFICE
Certificate

Patent No. PP18,441 P2 Patented: January 22, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: James Bryan Berry, Daphne, AL (US); and Thomas Dennis Meadows, Jr., Daphne, AL (US).

Signed and Sealed this Twentieth day of April 2010.

ANNE MARIE GRUNBERG
*Supervisory Patent Examiner*
Art Unit 1661